United States Patent
Chen et al.

(10) Patent No.: US 11,506,487 B2
(45) Date of Patent: Nov. 22, 2022

(54) X-RAY IMAGING METHOD AND SYSTEM THEREOF

(71) Applicant: Delta Electronics, Inc., Taoyuan (TW)

(72) Inventors: Sih-Yu Chen, Taoyuan (TW); Jhih-Shian Lee, Taoyuan (TW)

(73) Assignee: DELTA ELECTRONICS, INC., Taoyuan (TW)

(*) Notice: Subject to any disclaimer, the term of this patent is extended or adjusted under 35 U.S.C. 154(b) by 0 days.

(21) Appl. No.: 17/099,187

(22) Filed: Nov. 16, 2020

(65) Prior Publication Data

US 2021/0278205 A1 Sep. 9, 2021

(30) Foreign Application Priority Data

Mar. 6, 2020 (CN) .......................... 202010152161.8

(51) Int. Cl.
*G01B 15/02* (2006.01)
*G06T 7/60* (2017.01)
*A61B 6/00* (2006.01)

(52) U.S. Cl.
CPC .............. *G01B 15/025* (2013.01); *G06T 7/60* (2013.01); *A61B 6/544* (2013.01); *G06T 2207/10116* (2013.01)

(58) Field of Classification Search
CPC .............. G01B 15/025; G06T 7/60; G06T 2207/10116; A61B 6/544; A61B 6/5217; G01N 23/04; G01T 1/08
See application file for complete search history.

(56) References Cited

U.S. PATENT DOCUMENTS 5,309,495 A * 5/1994 Fischer .................. G01B 15/02
378/208
2003/0072409 A1 4/2003 Kaufhold et al.
2019/0175137 A1* 6/2019 Kappler ................ G01T 1/2985

FOREIGN PATENT DOCUMENTS

| CN | 109997029 A | 7/2019 | |
|---|---|---|---|
| EP | 2598100 B1 * | 8/2014 | ............. A61J 3/074 |
| JP | S-533262 A | 1/1978 | |
| JP | 2010249691 A | 11/2010 | |
| JP | 2013130392 A | 7/2013 | |

OTHER PUBLICATIONS

Office Action dated Jan. 6, 2021 in TW Application No. 109107443, 5 pages.
Extended European Search Report dated Apr. 30, 2021 in EP Application No. 20209588.1, 7 pages.
(Continued)

*Primary Examiner* — Kiho Kim
(74) *Attorney, Agent, or Firm* — Muncy, Geissler, Olds & Lowe, P.C.

(57) ABSTRACT

An X-ray imaging method includes the following steps: (a) performing a first object imaging and obtaining a first object intensity signal by detecting an X-ray passing through a first object; (b) performing baseline imaging process, obtaining a baseline intensity signal by detecting the X-ray when the first object is not in a FOV; and; (c) obtaining the first thickness of the first object by performing operations on the first object intensity signal, the baseline intensity signal, and the first attenuation coefficient of the first object.

11 Claims, 8 Drawing Sheets

(56) References Cited

OTHER PUBLICATIONS

CN Office Action of corresponding CN application No. 202010152161, 10 pages.
JP Office Action of corresponding JP application No. 2020-205759 with English machine translation, 12 pages.
Office Action dated Oct. 4, 2020 in JP Application No. 2020-205759, w/English-translation, 10 pages.

* cited by examiner

X-RAY IMAGING METHOD AND SYSTEM THEREOF

CROSS-BASELINE TO RELATED APPLICATION

The present application is based on, and claims priority from, China Application Serial Number CN202010152161.8, filed Mar. 6, 2020, the disclosure of which is hereby incorporated by baseline herein.

TECHNICAL FIELD

Technical Field

The present disclosure relates to an X-ray imaging method and system, and in particular it relates to a method and system for measuring the thickness, weight, and absorbed dose of an object by using X-rays.

BACKGROUND

In general, the current radiation dose measurement of objects requires the use of special and expensive dose measurement equipment, such as ion chamber, radiation dosimeter and proportional counter. This expensive dose-measurement equipment is installed on X-ray equipment or computed tomography scanner to measure the radiation dose will increase costs.

In addition, if a thermoluminescent dosimeter (TLD) is used for measurement, the immediate dose may not be obtained due to its principle. In addition, there are other ways to estimate radiation dose, such as applying the Monte Carlo simulation. However, it is quite time-consuming to calculate the dose and thickness of an object by the Monte Carlo simulation requiring a high-end computer.

SUMMARY

The present disclosure provides an X-ray imaging method. The X-ray imaging method includes the following steps: (a) performing a first object imaging process to obtain a first object intensity signal by detecting a plurality of X-rays passing through a first object; (b) performing a baseline imaging process to obtain a baseline intensity signal by detecting the X-rays when the first object is not in a FOV; and (c) obtaining the first thickness of the first object based on the first object intensity signal, the baseline intensity signal, and a first attenuation coefficient of the first object.

The present disclosure provides an X-ray imaging method. The X-ray imaging method includes the following steps: (a) performing a first object imaging process to obtain a first object intensity signal by detecting a plurality of X-rays passing through a first object; (b) performing a baseline imaging process to obtain a baseline intensity signal by detecting the X-rays when the first object is not in a FOV; (c) performing a second object imaging process to obtain a second object intensity signal by detecting the X-rays passing through a second object; (d) obtaining a sample intensity signal based on the first object intensity signal and the second object intensity signal, wherein the first object is a carrier, and the second object comprises a sample and the carrier; and (e) obtaining a sample thickness based on the sample intensity signal, the baseline intensity signal and a sample attenuation coefficient.

The present disclosure provides an X-ray imaging system. The X-ray imaging system includes an X-ray source, a detector and a processor. The X-ray source is configured to perform a first object imaging process so that a plurality of X-rays pass through a first object placed in a field of view (FOV) and perform a baseline imaging process as the first object is not in the FOV. The detector is configured to obtain a baseline intensity signal in the baseline imaging process and obtain a first object intensity signal in the first object imaging process. And, the processor is coupled to the detector. The processor is configured to operate instructions, comprising: calculating a first thickness of the first object based on the first object intensity signal, the baseline intensity signal, and a first attenuation coefficient of the first object.

DETAILED DESCRIPTION

The following description is of the best-contemplated mode of carrying out the invention. This description is made for the purpose of illustrating the general principles of the invention and should not be taken in a limiting sense. The scope of the invention is best determined by baseline to the appended claims.

The present invention will be described with respect to particular embodiments and with baseline to certain drawings, but the invention is not limited thereto and is only limited by the claims. It will be further understood that the terms "comprises," "comprising," "comprises" and/or "including," when used herein, specify the presence of stated features, integers, steps, operations, elements, and/or components, but do not preclude the presence or addition of one or more other features, integers, steps, operations, elements, components, and/or groups thereof.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Figure 1:
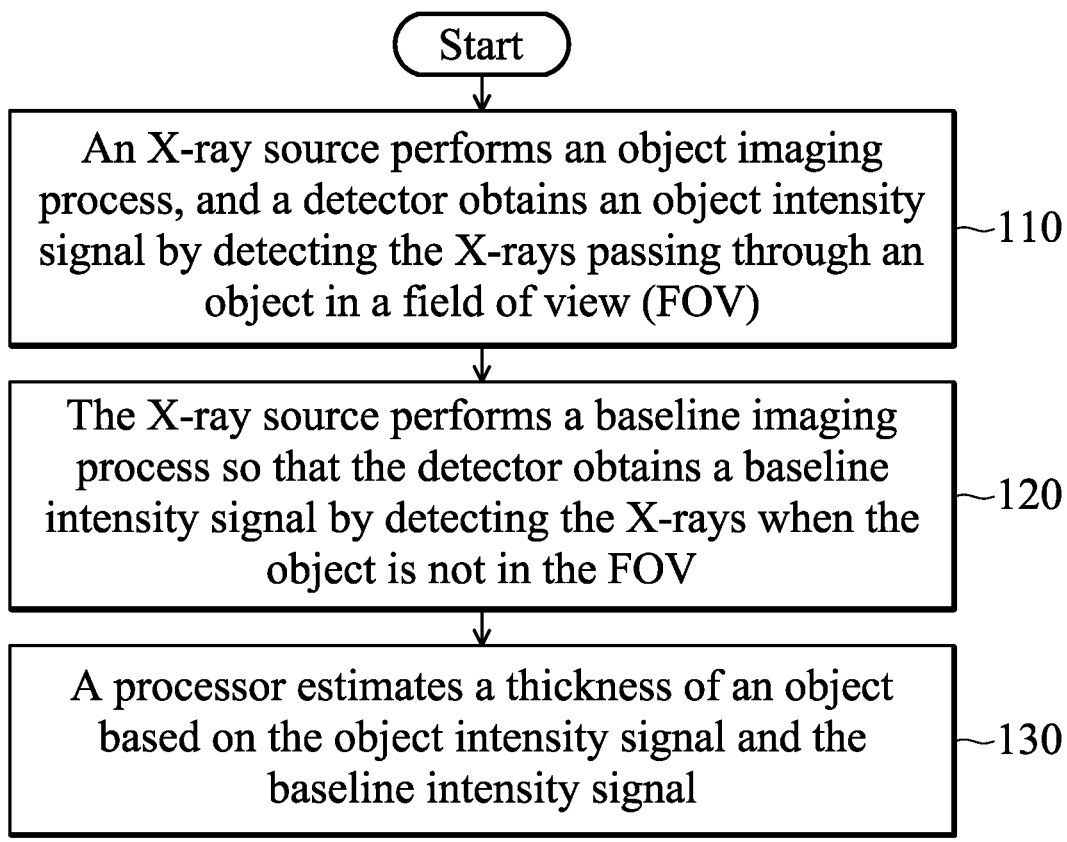
FIG. 1 is a flowchart of an X-ray imaging method in accordance with one embodiment of the present disclosure.
Figure 2:
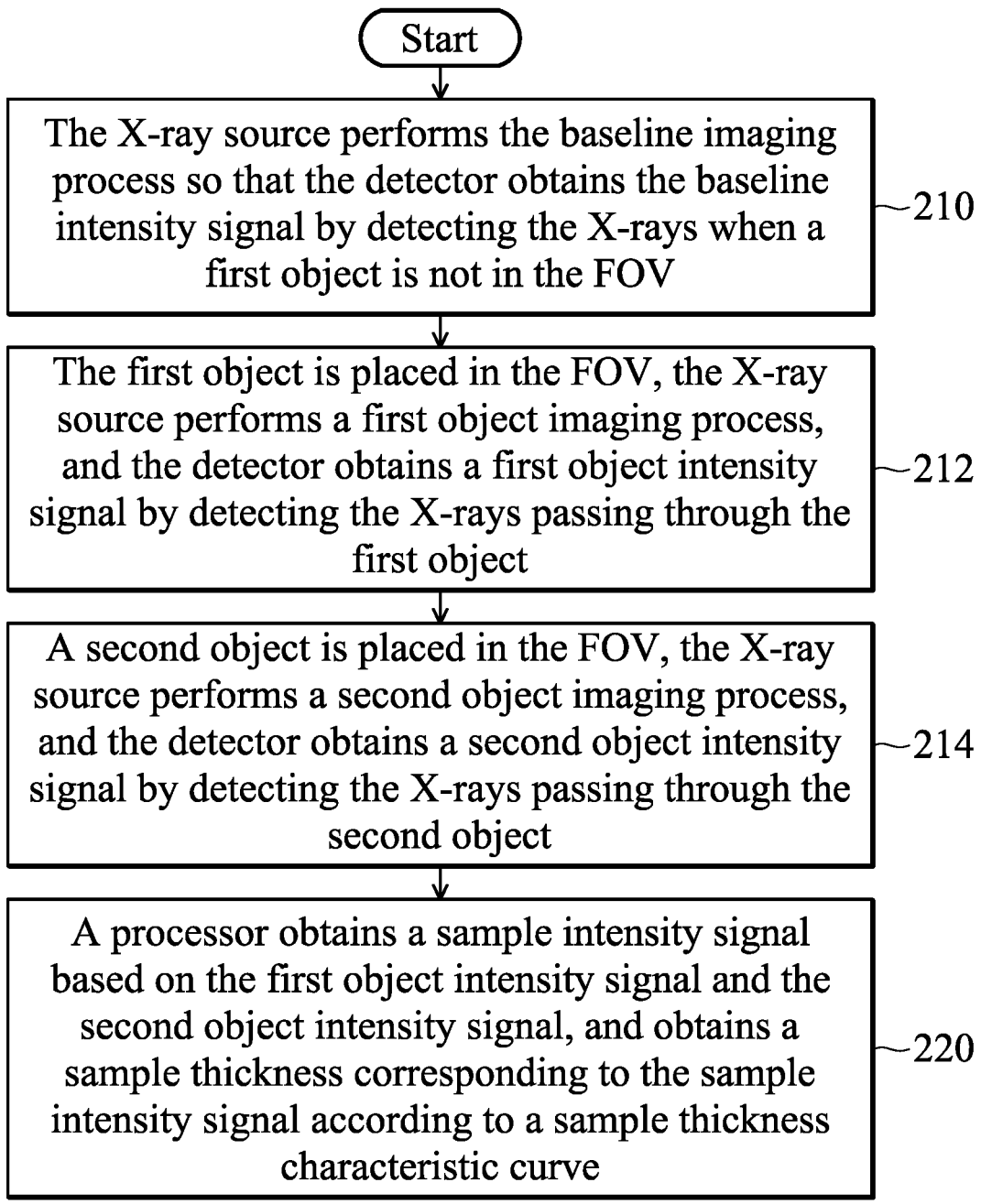
FIG. 2 is a flowchart of an X-ray imaging method in accordance with one embodiment of the present disclosure.
Figure 3A:
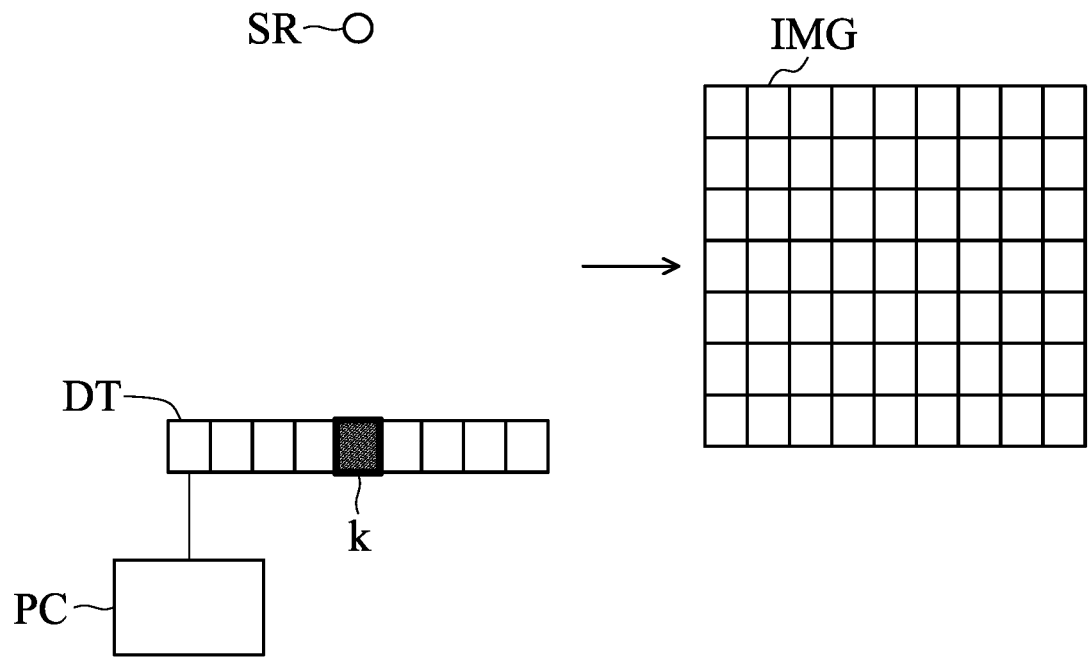
FIGS. 3A-3C are schematic diagrams of an X-ray imaging system in accordance with one embodiment of the present disclosure.
Figure 3B:
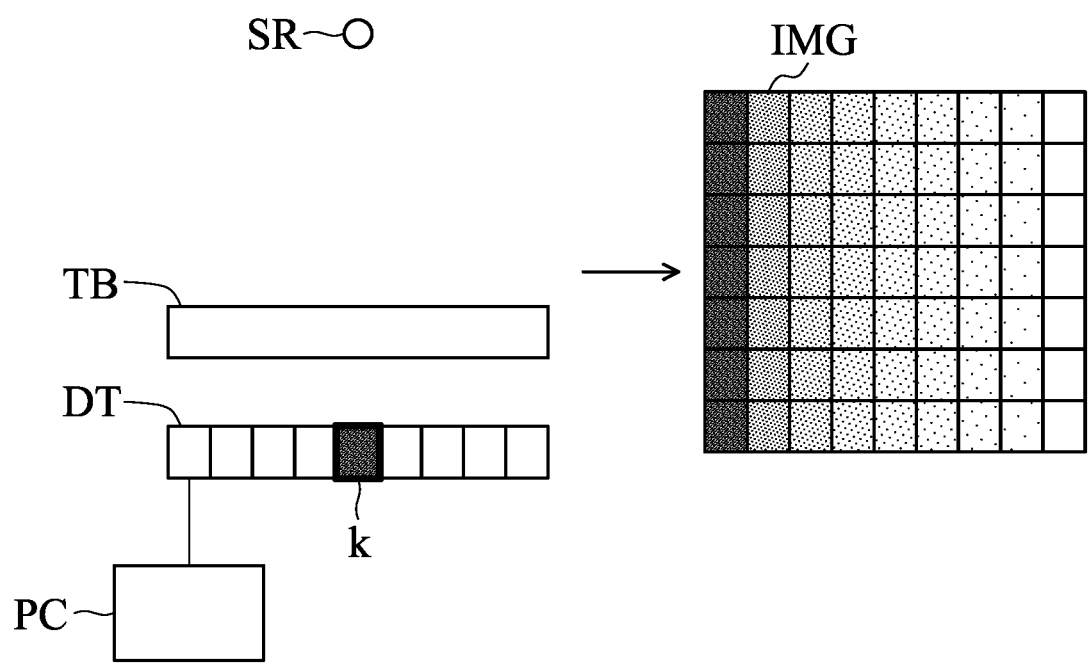
Figure 3C:
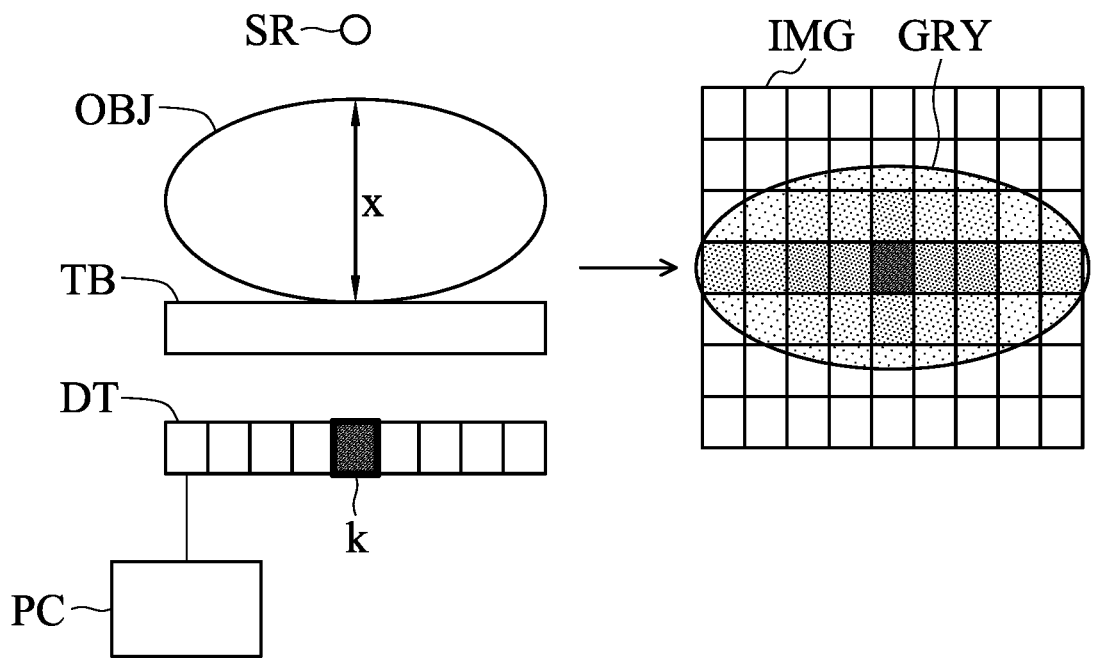

Please refer to FIGS. 1, 2, 3A-3C, FIG. 1 is a flowchart of an X-ray imaging method 100 in accordance with one embodiment of the present disclosure. FIG. 2 is a flowchart of X-ray imaging method 200 in accordance with one embodiment of the present disclosure. FIGS. 3A-3C are schematic diagrams of an X-ray imaging system in accordance with one embodiment of the present disclosure.

Please refer to FIG. 3A. In FIG. 3A, the X-ray imaging system includes at least an X-ray source SR, a detector DT, and a processor PC.

In one embodiment, the X-ray source SR is used to generate a plurality of X-rays.

In an embodiment, the detector DT is correspondingly arranged in the direction of the X-rays emitted by the X-ray source SR. In addition, the detector DT is used to detect X-rays passing through medium (such as gas, solid, or liquid).

In an embodiment, the processor PC is used to operate instructions. The processor PC can also be implemented by a microcontroller, a microprocessor, a digital signal processor, an application specific integrated circuit (ASIC) or a logic circuit, but is not limited thereto.

The flow of the X-ray imaging method 100 will be described below with baseline to FIG. 1.

In step 110, an X-ray source SR performs an object imaging process, and a detector DT obtains an object intensity signal by detecting the X-rays passing through an object in a field of view (FOV).

In one embodiment, when the X-ray source SR performs the object imaging process so that the detector DT obtains the object intensity signal, and transmits the object intensity signal to the processor PC. The object intensity signal can be an X-ray image, and the X-ray image can be presented by a two-dimensional projection image IMG.

In one embodiment, the processor PC is coupled to the detector DT. In addition, the processor PC is configured to receive the object intensity signal generated by the detector DT.

In step 120, the X-ray source SR performs a baseline imaging process, and the detector DT obtains a baseline intensity signal by detecting the X-rays when the object is not in the FOV.

In step 130, a processor PC estimates a thickness of an object based on the object intensity signal and the baseline intensity signal.

In one embodiment, the object described in FIG. 1 can be a carrier. In another embodiment, the object described in FIG. 1 can be a combination of a carrier and a sample (in other words, a combination of sample(s) and the carrier is regarded as the object described in FIG. 1). In one embodiment, the object described in step 120 is not in the FOV, which means that the carrier and sample are not placed in the FOV, and the X-rays are directly shot to the detector DT, so as to capture a baseline image.

The following describes the three types of imaging cases in detail, such as blank image (the object is not in the FOV), the object is the carrier TB (hereinafter referred to as the first object), and the object is the combination of the carrier TB and the sample OBJ (hereinafter referred to as the second object). However, the definition of the first object and the second object in the present invention is not limited thereto.

In step 210, the X-ray source SR performs the baseline imaging process so that the detector DT obtains the baseline intensity signal by detecting the X-rays when a first object is not in the FOV.

In one embodiment, as shown in FIG. 3A, no object is placed in the FOV. The detector DT detects the X-rays when the object is not in the FOV, such as the sample and the carrier TB are not in the FOV and the baseline imaging process is performed by the X-ray imaging system to obtain a baseline intensity signal. The baseline intensity signal is also called a blank image. The distribution of the number of X-ray photons in the energy range of the X-ray source is called X-ray energy spectrum (see FIG. 4). The X-ray energy spectrum can be obtained by a known lookup table, measurement or calculation. The baseline intensity signal obtained by the detector DT is an intensity value which is the sum of the X-rays received by the detector DT under the X-ray energy spectrum.

In step 212, the first object (such as the carrier TB) is placed in the FOV. As shown in FIG. 3B, the X-ray source SR performs a first object imaging process, and the detector DT obtains a first object intensity signal by detecting the X-rays passing through the first object.

More specifically, the X-ray source SR provides the X-rays and shoot the first object. Then the detector DT obtains the first object intensity signal, and transmits the first object intensity signal to the processor PC.

In step 214, as shown in FIG. 3C, a second object (such as a combination of the carrier TB and the sample OBJ) is placed in the FOV. The X-ray source SR performs a second object imaging process. The detector DT obtains a second object intensity signal by detecting the X-rays passing through the second object.

More specifically, the sample OBJ is set on the carrier TB, the X-ray source SR radiograph the carrier TB and the sample OBJ. Then, the detector DT obtains the second object intensity signal, and transmits the second object intensity signal to the processor PC. The first object intensity signal and the second object intensity signal are X-ray photon signals. As shown in the manner of the two-dimensional projection image IMG in FIG. 3C, the gray-scale block GRY in the two-dimensional projection image IMG represents an X-ray block passing through the second object.

In one embodiment, for example, if a pixel k of the detector DT receives the lowest amount of the X-rays when the second object imaging process is performed, the thickest portion of the sample OBJ is positioned corresponding to the pixel k.

The above steps 210 to 214 are not limited in sequence. In one embodiment, the area where the detector DT receives the X-rays is referred to the FOV.

In step 220, a processor PC obtains a sample intensity signal based on the first object intensity signal and the second object intensity signal, and obtains a sample thickness x corresponding to the sample intensity signal according to a sample thickness characteristic curve. In one embodiment, the processor PC subtracts the first object intensity signal from the second object intensity signal to obtain the sample intensity signal.

In one embodiment, the processor PC obtains the sample thickness characteristic curve according to the baseline intensity signal, the X-ray energy spectrum, and a sample attenuation coefficient.

In one embodiment, the thickness characteristic curve, for examples, a sample thickness characteristic curve, a first thickness characteristic curve, and a second thickness characteristic curve, which can be calculated by the following function (1) Beer-Lambert Law.

In one embodiment, the thickness characteristic curve is obtained based on the calculation of the baseline intensity signal, the X-ray energy spectrum and the attenuation coefficient. The operation includes the results of discrete multiplication, and then sum the results of discrete multiplication.

In one embodiment, using a certain imaging parameters set (including the voltage and the current of the X-ray source SR or different types of filters, etc.), a two-dimensional projection blank image is captured as no object in the FOV, that is, the detector DT obtains the baseline intensity signal. Then, an object of any known material, such as water, laboratory animals, acrylic, etc., is placed in the FOV. Using the same imaging parameters set, a two-dimensional projection image of an object (the following object can refer to the first object or the second object) is captured, that is, the detector DT obtains the object intensity signal. Through the following function (1) calculation, a thickness of the object can be estimated from the signals obtained by the detector DT.

$$N_1 = \sum_{i=1\,keV}^{E\,keV} N_{0_i} e^{-\mu_i x} \quad (1)$$

The symbol $N_{0_i}$ represents the intensity value of the baseline intensity signal for a pixel, and is the number of photons at a specific energy i of the X-ray energy spectrum provided by the X-ray source. The symbol μ represents the attenuation coefficient of an object of known material. According to different values of X-ray energy of the spectrum, the attenuation coefficient will be a different value, and the attenuation coefficient can be a linear attenuation coefficient. The symbol $N_1$ represents the intensity value obtained by the detector DT after the object is placed in the FOV. The symbol x represents the thickness of the object positioned corresponding to a pixel of the detector DT. Therefore, by using the intensity signal obtained from the image detector DT, the processor PC can acquire the object thickness by the thickness characteristic curve.

Figure 4:
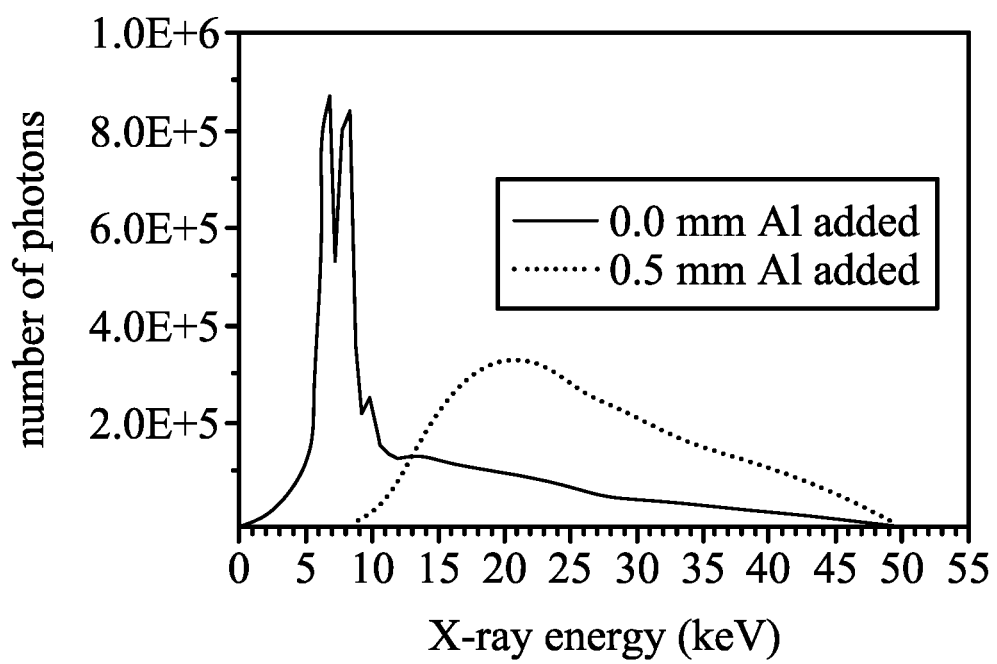
FIG. 4 is a graph of the X-ray energy-photon number in accordance with one embodiment of the present disclosure.
Figure 5:
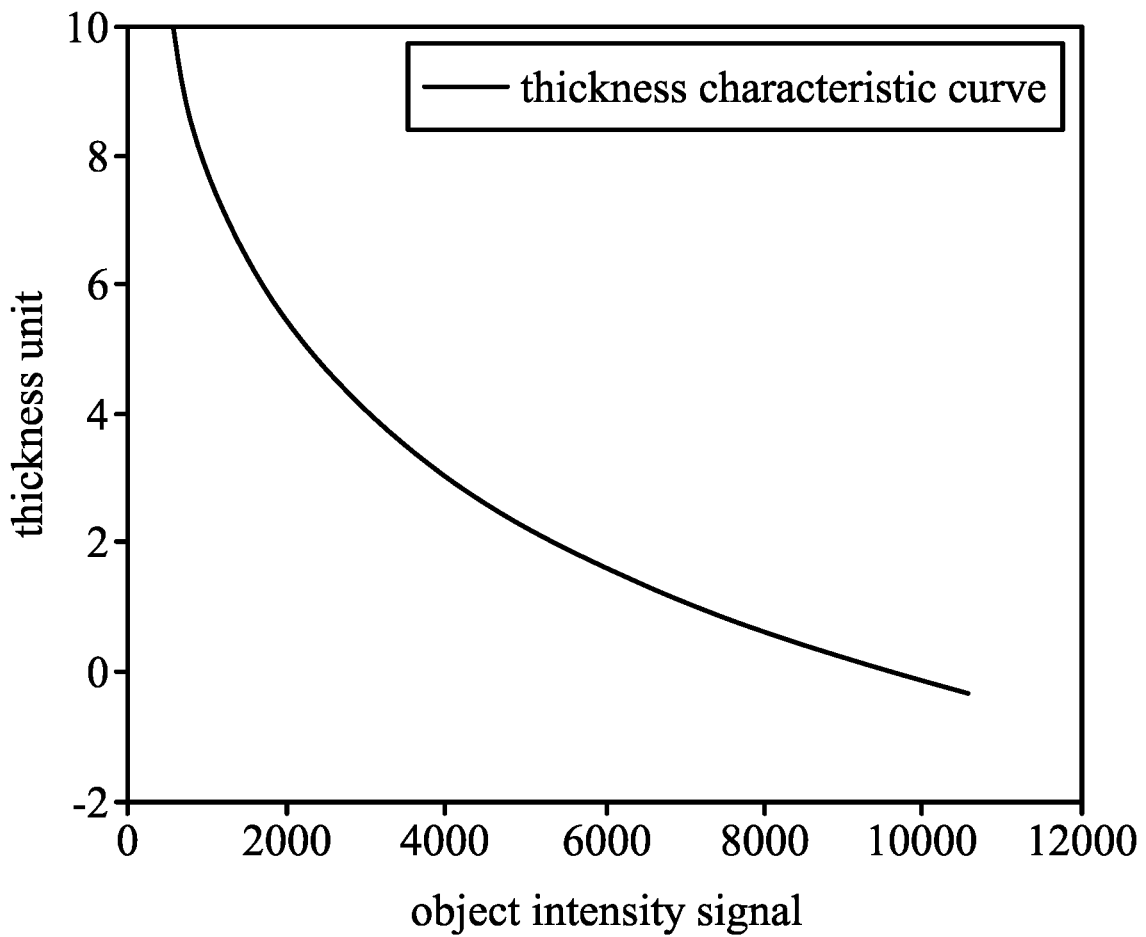
FIG. 5 is a graph of a thickness characteristic curve in accordance with one embodiment of the present disclosure.

More specifically, the above function (1) can be expanded into function (2). FIG. 4 is a graph of the X-ray energy-photon number in accordance with one embodiment of the present disclosure. The processor PC imports the X-ray energy spectrum into Beer's Law. As shown in FIG. 4, the horizontal axis represents the X-ray energy and the vertical axis represents the number of photons. The X-ray energy spectrum will have different photon flux distributions according to the filter material, filter thickness and the maximum voltage of X-ray source. As shown in FIG. 4, the solid line represents the energy spectrum of the X-ray source with the maximum voltage value of 50 keV and without a filter. The dotted line represents the energy spectrum of the X-ray source with the maximum voltage value of 50 keV with 0.5 mm aluminum filter. The processor PC estimates the spectral distribution of the pixels by simulating, calculating or measuring the X-ray energy spectrum with the selected imaging parameters including the energy of the X-ray source, the current of the X-ray source, or types of filters. More specifically, a curve of the object thickness and the object intensity signal, that is the thickness characteristic curve, can be obtained by the following function (2) as shown in FIG. 5. FIG. 5 is a graph of a thickness characteristic curve in accordance with one embodiment of the present disclosure.

$$N_1 = \sum_{i=1\,keV}^{E\,keV} N_{0_{i\,keV}} e^{-\mu_i x} = N_{0_{1\,keV}} e^{-\mu_{1kev} x} + N_{0_{2\,keV}} e^{-\mu_{2kev} x} + N_{0_{3\,keV}} e^{-\mu_{3kev} x} + N_{0_{4\,keV}} e^{-\mu_{4kev} x} + \ldots N_{0_{E\,keV}} e^{-\mu_{Ekev} x} \quad (2)$$

The symbol μ represents the attenuation coefficient of the object, which has different values according to the X-ray energy of the spectrum. The symbol i represents the specific energy of the X-ray energy spectrum (from 1 keV to the maximum voltage value set by the X-ray source). The symbol x represents the thickness of the object positioned corresponding to a pixel.

FIG. 5 is a graph of a thickness characteristic curve in accordance with one embodiment of the present disclosure. The solid line in FIG. 5 is the thickness characteristic curve of the function (2), the horizontal axis of FIG. 5 represents the object intensity signal, and the vertical axis represents the thickness (the unit is, for example, cm). Therefore, the processor PC can obtain the object thickness x according to the detected object intensity signal in the thickness characteristic curve of the function (2) in the step 220. In one embodiment in the step 220, $N_1$ of the function (2) represents an intensity value of the sample intensity signal for the pixel.

Figure 6:
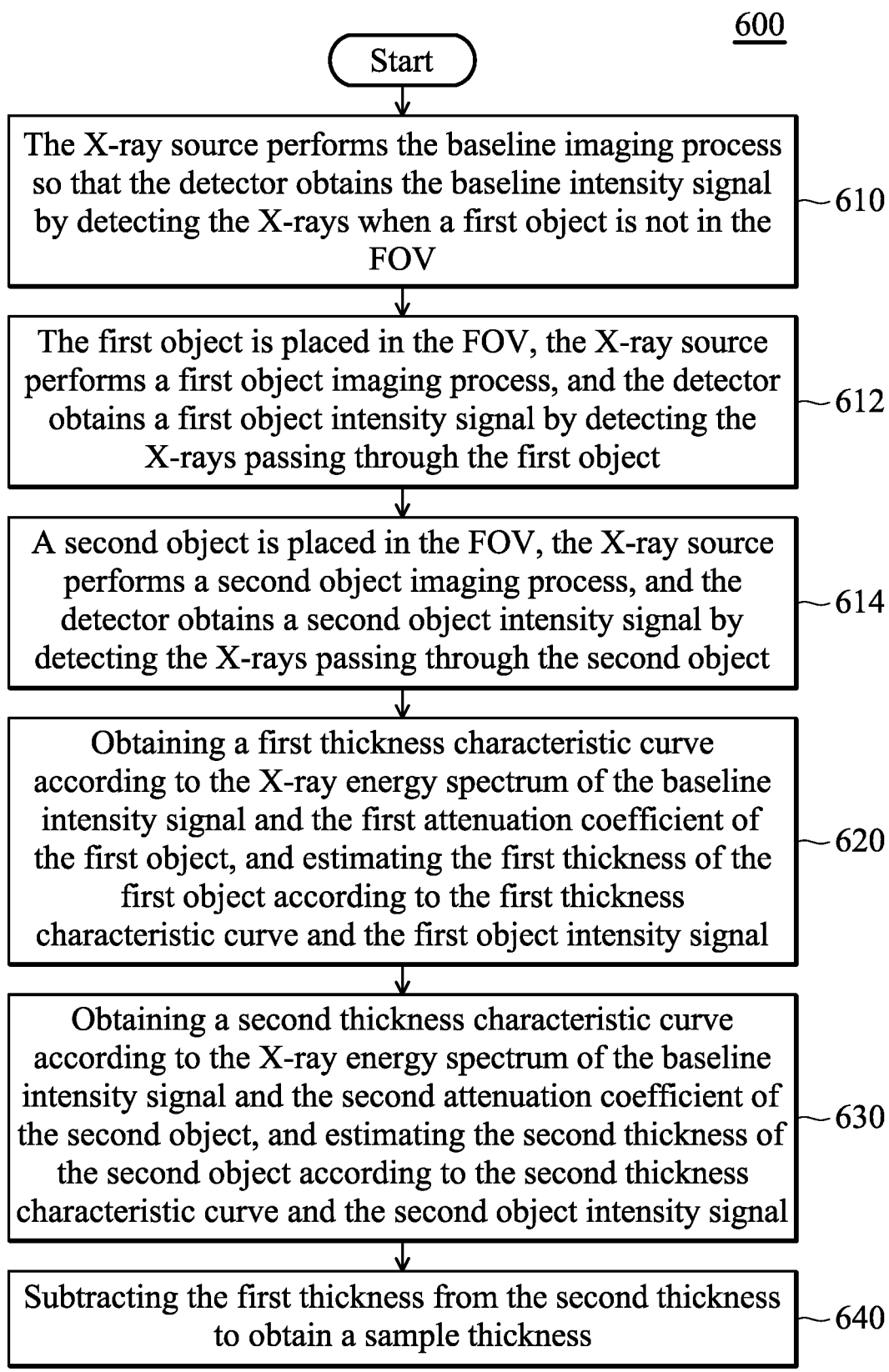
FIG. 6 is a flowchart of a method 600 for calculating the thickness of an object using X-rays in accordance with one embodiment of the present disclosure.

Please refer to FIG. 6, FIG. 6 is a flowchart of a method 600 for calculating the thickness of an object using X-rays in accordance with one embodiment of the present disclosure. Steps 610, 612, and 614 in FIG. 6 are the same as steps 210, 212, and 214 in FIG. 2, respectively, and therefore will not be described again.

In one embodiment, the processor PC executes estimating a first thickness of the first object based on the first object intensity signal and the baseline intensity signal. More specifically, in step 620, the processor PC obtains the first thickness characteristic curve according to the X-ray energy spectrum of the baseline intensity signal and the first attenuation coefficient of the first object. Besides, $N_1$ of the function (2) represents an intensity value of the first object intensity signal for the pixel. In addition, the processor PC estimates the first thickness of the first object according to the first thickness characteristic curve and the first object intensity signal.

In one embodiment, the processor PC executes the estimation of a second thickness of the second object based on the second object intensity signal and the baseline intensity signal. More specifically, in step 630, the processor PC obtains a second thickness characteristic curve according to the X-ray energy spectrum of the baseline intensity signal and the second attenuation coefficient of the second object. Besides, $N_1$ of the function (2) represents an intensity value of the second object intensity signal for the pixel. In addition, the processor PC estimates the second thickness of the second object according to the second thickness characteristic curve and the second object intensity signal.

In step 640, the processor PC subtracts the first thickness from the second thickness to obtain a sample thickness. The first object includes a carrier TB, and the second object includes a sample OBJ and the carrier TB.

In one embodiment, if the object material (such as the sample OBJ) is known, the density od of the object is also known. In addition, the body thickness x of the sample OBJ can be obtained from the above function. Further, the area of the sample (pixel size) corresponding to the pixel k can be calculated by the area of the pixel k. The following formula (3) can be used to calculate the weight per pixel ($w_k$) of the sample corresponding to the pixel k.

$$w_k = (psL * psW) * x * od \quad (3)$$

$$\text{Object weight} = \sum_{k=1}^{maximum\,detector\,pixel\,number} w_k \quad (4)$$

The symbol $w_k$ represents the weight of the sample having the thickness x corresponding to the pixel k, and the unit is kilogram or gram. The symbol psL represents the length (in cm or m) of the pixel size. The symbol psW represents the width (in cm or m) of the pixel size. The symbol od represents the density of the sample, and the unit is kg/m³ or g/cm³. Then, according to the function (4), the weight w k of the sample corresponding to all of the pixels are added to obtain the total weight of sample in the FOV.

Based on the above steps, the processor PC estimates the total weight of sample in the FOV based on the thickness x, the density, and the pixel size of the sample.

Figure 7:
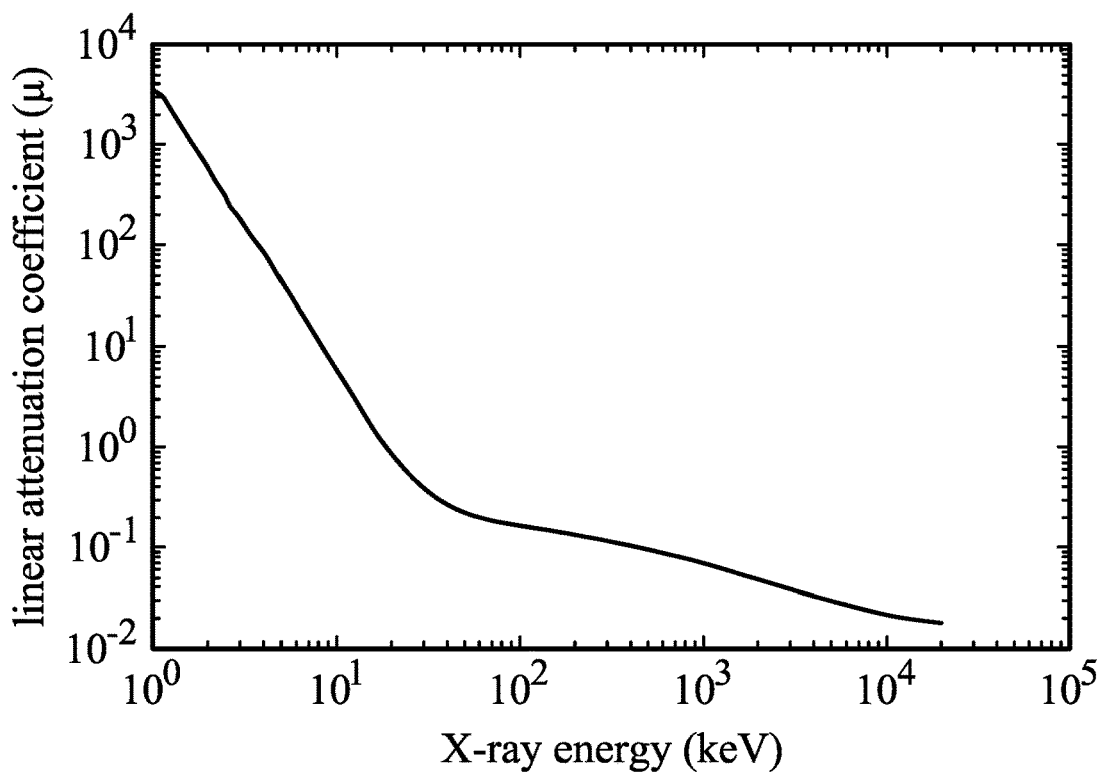
FIG. 7 is a graph of the attenuation coefficient in accordance with one embodiment of the present disclosure.

For example, after the processor PC receives the baseline intensity signal (blank image), the above function (1) is used to import the X-ray energy spectrum, the sample (linear) attenuation coefficient, and the baseline intensity signal to obtain a sample thickness characteristic curve. The attenuation coefficient is shown in FIG. 7. FIG. 7 is a graph of the attenuation coefficient in accordance with one embodiment of the present disclosure. The horizontal axis represents X-ray energy (keV), and the vertical axis represents the linear attenuation coefficient (μ). The unit of the linear attenuation coefficient is cm⁻¹. The X-ray imaging system obtains the sample thickness characteristic curve through the step 220 above, and obtains the sample thickness x corresponding to the sample intensity signal according to the sample thickness characteristic curve, and imports the sample thickness x, the sample density and the pixel size into the function (3). Then the sample weight (sample pixel size*sample thickness*sample density=sample weight) corresponding to the pixel k can be obtained. To sum of each sample weight per pixel is the total weight of sample in the FOV.

In one embodiment, the X-ray imaging system can further calculate the absorbed dose of the object after the total weight of sample in the FOV is obtained. When the values imported in the following functions (5) and (6) are parameters of the carrier TB and/or the sample OBJ, the absorbed dose of the carrier TB and/or the sample OBJ will be calculated correspondingly. The following takes the calculation of the sample absorbed dose as an example.

In an embodiment, the number of photons absorbed by the sample can be calculated by the following functions (5)-(6).

$$\sum_{i=1\,keV}^{E\,keV} N_{1_{en_i}} = \sum_{i=1\,keV}^{E\,keV} N_{0_{en_i}} e^{-\mu_{en_i} x} \quad (5)$$

$$N_{abs_i} = N_{0_{en_i}} - N_{1_{en_i}} \quad (6)$$

Figure 8:
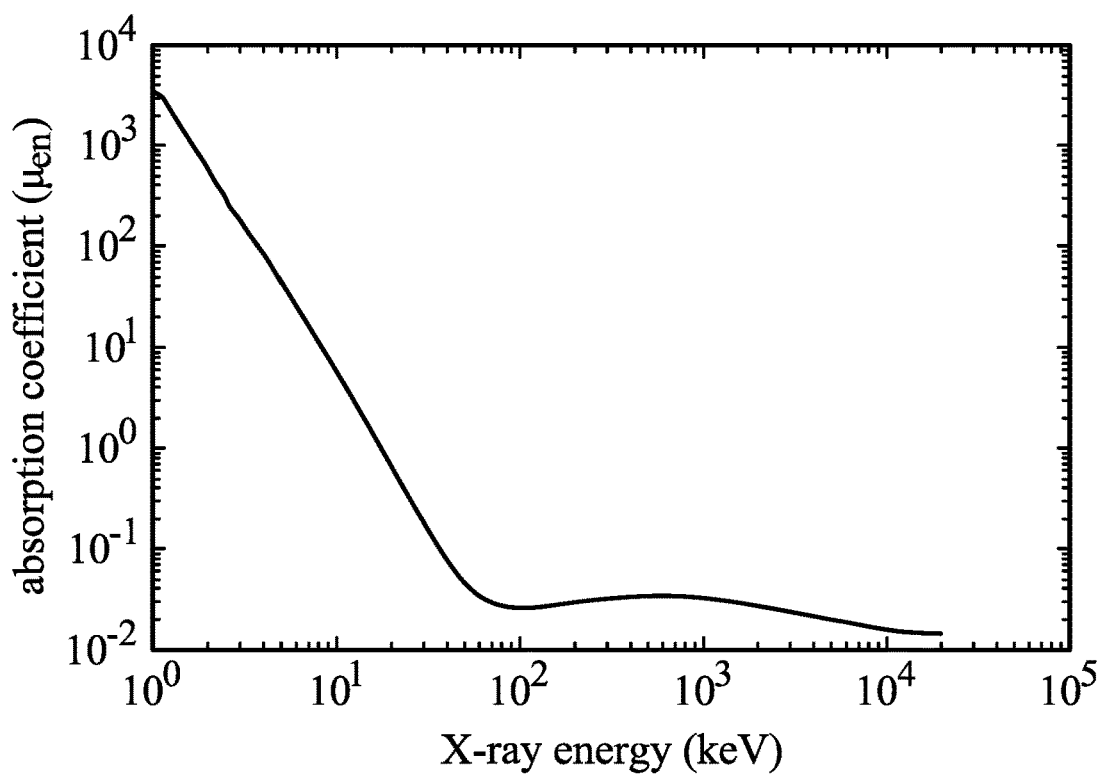
FIG. 8 is a graph of the sample absorption coefficient in accordance with one embodiment of the present disclosure.

$N_{1\,en_i}$ is the number of residual photons which are not absorbed by the sample after the X-rays of specific energy i of the X-ray energy spectrum pass through the sample along the sample thickness x, and the unit is count. $N_{0\,en_i}$ is the baseline intensity signal for one pixel and the unit is count. This pixel is, for example, the pixel k in FIG. 3C, symbol i is the specific energy of the X-ray energy spectrum, and the maximum value is E (the unit is keV). $N_{abs_i}$ is the number of absorbed photons in the sample as the X-rays pass through the sample along the thickness x at a specific energy i. $\mu_{en_i}$ is the absorption coefficient of the sample. $\mu_{en}$ has different values according to the X-ray energy i. Please refer to FIG. 8, a graph of the sample absorption coefficient in accordance with one embodiment of the present disclosure. The horizontal axis of FIG. 8 represents X-ray energy (keV), and the vertical axis represents the absorption coefficient ($\mu_{en}$) of the sample. According to this, the processor PC can calculate the number of residual photons which are not absorbed by the sample according to the baseline intensity signal, the sample absorption coefficient, and the sample thickness. The processor PC subtracts the number of residual photons from the baseline intensity signal, thereby knowing the number of photons absorbed by the sample.

In one embodiment, the X-ray imaging system calculates the number of absorbed photons in the sample at the specific energy i of the X-ray energy spectrum for the pixel k (as shown in FIG. 3C). The number of absorbed photons per pixel of the sample at the specific energy i of the X-ray energy spectrum can be converted into the absorbed energy per pixel by the function (7), and the average absorbed dose of the sample can be calculated by the function (8) (unit: Gy, J/kG):

$$\text{Absorbed Energy}_k = \sum_{i=1}^{E\,keV} i \times N_{abs_i} \times \left(\frac{1.6 \times 10 - 13\,\text{J}}{keV}\right) \quad (7)$$

$$\text{Object Dose} = \text{J/kg} = \frac{\sum_{k=1}^{maximum\,detector\,pixel\,number} \text{Absorbed Energy}_k}{\text{Object weight}} \quad (8)$$

The symbol E is the maximum voltage of the X-ray source. The symbol i is the specific energy of the X-ray energy spectrum, and the maximum value is E (unit: keV). The symbol $N_{abs_i}$ is the number of photons absorbed by the sample as the X-rays pass through the sample along the thickness x at a specific energy i of the X-ray energy spectrum. The symbol Object weight is the total weight of sample in the FOV detected and calculated by the X-rays imaging system, and its unit is kilogram. The string "detector pixel number" is the number of pixels in the two-dimensional projection image IMG in FIG. 3A. Therefore, the processor PC can obtain the absorbed energy of the sample along the thickness x corresponding to the pixel k according to the number of absorbed photons. The processor PC then calculates the sum of the absorbed energy of all pixels for the sample in the FOV.

Figure 9:
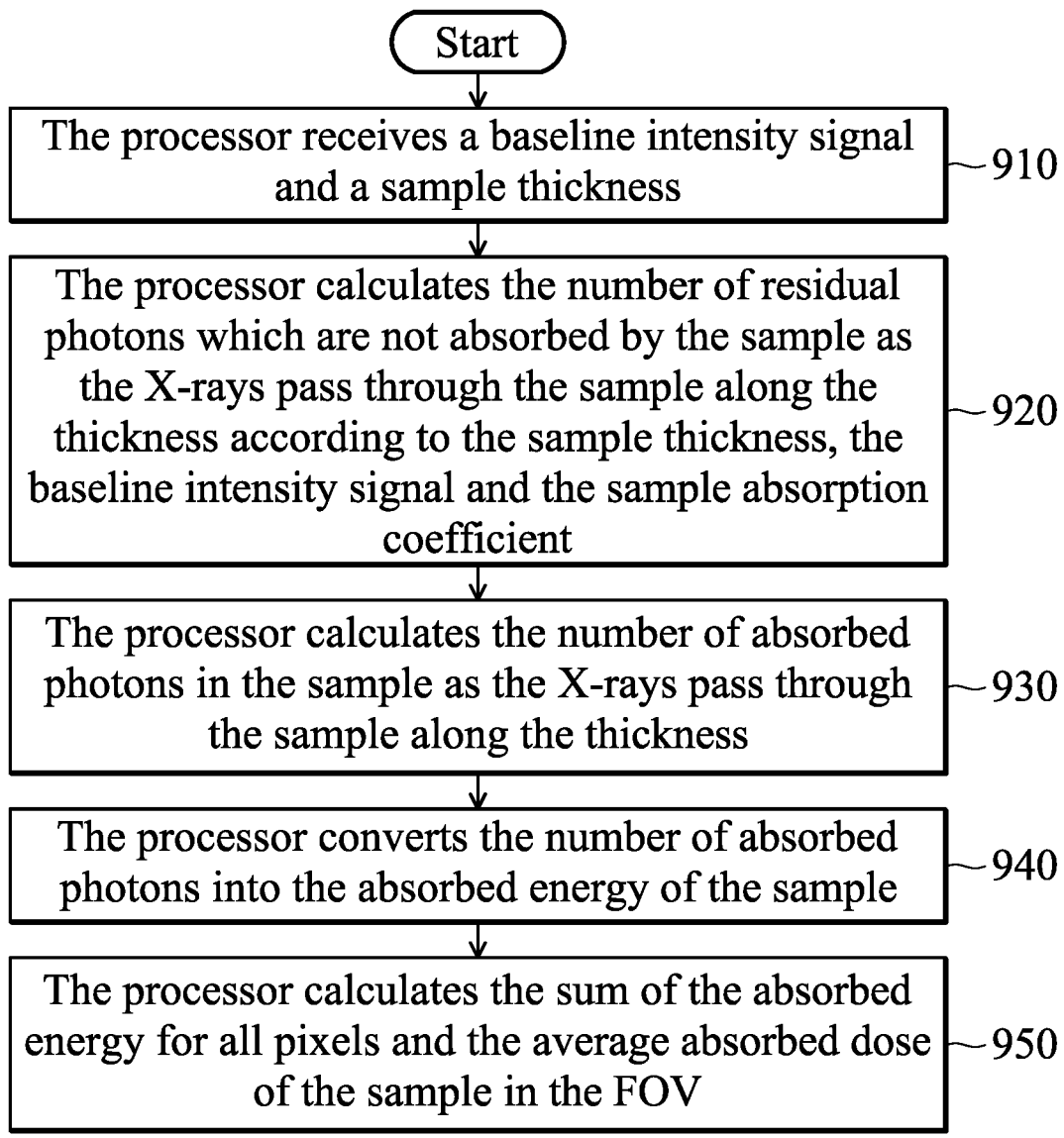
FIG. 9 is a flowchart of a method for calculating a sample absorbed dose in accordance with one embodiment of the present disclosure.

In one embodiment, please refer to FIG. 9, FIG. 9 is a flowchart of a method 900 for calculating a sample absorbed dose in accordance with one embodiment of the present disclosure.

In step 910, the processor PC receives a baseline intensity signal and a sample thickness.

In step 920, the processor PC calculates the number of residual photons which are not absorbed by the sample as the X-rays pass through the sample along the thickness x, the baseline intensity signal and the sample absorption coefficient. In one embodiment, the processor PC applies the function (5) to calculate the number of residual photons per pixel as the X-rays at a specific energy i of the X-ray energy spectrum pass through the sample along the thickness x.

In step 930, the processor PC calculates the number of absorbed photons in the sample as the X-rays pass through the sample along the thickness x. In one embodiment, the processor PC applies the function (6) to calculate the number of absorbed photons per pixel as the X-rays pass through the sample along the thickness x at a specific energy i of the X-ray energy spectrum.

In step 940, the processor PC converts the number of absorbed photons into the absorbed energy of the sample. In one embodiment, the processor PC applies function (7) to calculate the absorbed energy per pixel.

In step 950, the processor PC calculates the sum of the absorbed energy for all pixels and the average absorbed dose of the sample in the FOV. In one embodiment, the processor PC applies the function (8) to calculate the average absorbed dose of the sample in the FOV.

In one embodiment, the X-ray imaging system can calculate the X-ray dose rate emitted by the X-ray source SR by the method 900, such as simulating a sample as a ion chamber (not shown). The free cavity of the ion chamber is filled with air, for example, the known free cavity thickness x and the sample absorption coefficient (air absorption coefficient) are imported into the functions (3) to (8). Therefore the average absorbed dose of the ion chamber is obtained. Then the X-ray radiation dose rate emitted by the X-ray source SR can be obtained based on the average absorbed dose.

The X-ray imaging method and system shown in the present invention calculate the object thickness, the average absorbed dose and the radiation dose according to the intensity signals on the detector. Through the calculations, the thickness and weight of the object and the radiation dose absorbed in the object can be known directly from the X-ray image. This technology can be applied to instantly provide the dose rate, cumulative dose delivered by the current X-ray source, and the average dose absorbed by the object. In practical applications, the operator can know the thickness of the object through X-ray imaging and can know the current X-ray dose rate and the average dose absorbed by the object without additional expensive dose measurement equipment.

The method of the present invention, or a specific form or part thereof, may exist in the form of a code. The code can be included in physical media, such as floppy disks, CD-ROMs, hard disks, or any other machine-readable (such as computer-readable) storage media, or is not limited to external forms of computer program products. When the code is loaded and executed by a machine, such as a computer, the machine becomes a device for participating in the present invention. The code can also be transmitted through some transmission media, such as wire or cable, optical fiber, or any transmission type. When the code is received, loaded, and executed by a machine, such as a computer, the machine becomes a device for participating in the present invention. When implemented in a general-purpose processing unit, the code in combination with the processing unit provides a unique device that operates similar to an application-specific logic circuit.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such a feature may be combined with one or more other features of the other implementations as may be desired and advantageous for any given or particular application.

What is claimed is:

1. An X-ray imaging method, comprising:
    (a) performing a first object imaging process to obtain a first object image by detecting a plurality of X-rays of a X-ray source passing through a first object in an field of view (FOV);
    (b) performing a baseline imaging process to obtain a baseline image by detecting the X-rays when the first object is not in the FOV;
    (c) obtaining a first thickness of the first object based on the first object image, the baseline image, and a first attenuation coefficient of the first object;
    (d) performing a second object imaging process to obtain a second object image by detecting the X-rays passing through a second object in the FOV;
    (e) obtaining a second thickness of the second object based on the second object image, the baseline image, and a second attenuation coefficient of the second object;
    (f) subtracting the first thickness from the second thickness to obtain a sample thickness, wherein the first object is a carrier, the second object comprises a sample and the carrier;
    (g) obtaining a number of residual photons base on the baseline image, the sample thickness, and a sample absorption coefficient; and
    (h) obtaining the number of absorbed photons in the sample based on the baseline image and the number of residual photons.

2. The X-ray imaging method of claim 1, wherein obtaining the first thickness in step (c) further comprises:
    (c-1) calculating an X-ray energy spectrum of the baseline image and the first attenuation coefficient to obtain a first thickness characteristic curve; and
    (c-2) obtaining the first thickness based on the first thickness characteristic curve and the first object image.

3. The X-ray imaging method of claim 2, wherein the first thickness characteristic curve is obtained through a function, and the function includes:

$$N_1 = \sum_{i=1\,keV}^{E\,keV} N_{0_i\,keV} e^{-\mu_i x} = N_{0_1\,keV} e^{-\mu_{1kev}x} + N_{0_2\,keV} e^{-\mu_{2kev}x} + N_{0_3\,keV} e^{-\mu_{3kev}x} + N_{0_4\,keV} e^{-\mu_{4kev}x} + \ldots N_{0_{E\,keV}} e^{-\mu_{Ekev}x}$$

Wherein $N_{0_1}$ represents an intensity value of the baseline image for a pixel, $N_1$ represents an intensity value of the first object image for the pixel, E represents a maximum voltage of the X-ray source, μ represents the first attenuation coefficient, i represents a specific energy of the X-ray energy spectrum, and x represents the first thickness corresponding to the pixel.

4. The X-ray imaging method of claim 1, wherein obtaining the second thickness in step (e) comprises:
    (e-1) obtaining a second thickness characteristic curve based on the X-ray energy spectrum of the baseline image and the second attenuation coefficient; and
    (e-2) obtaining the second thickness based on the second thickness characteristic curve and the second object image.

5. The X-ray imaging method of claim 4, wherein the second thickness characteristic curve is obtained through a function, and the function includes:

$$N_1 = \sum_{i=1\,keV}^{E\,keV} N_{0_{i\,keV}} e^{-\mu_i x} = N_{0_{1\,keV}} e^{-\mu_{1\,keV} x} + N_{0_{2\,keV}} e^{-\mu_{2\,keV} x} +$$

$$N_{0_{3\,keV}} e^{-\mu_{3\,keV} x} + N_{0_{4\,keV}} e^{-\mu_{4\,keV} x} + \ldots N_{0_{E\,keV}} e^{-\mu_{E\,keV} x}$$

Wherein $N_{0_i}$ represents an intensity value of the baseline image for a pixel, $N_1$ represents an intensity value of the second object image for the pixel, E is a maximum voltage of the X-ray source, μ represents the second attenuation coefficient, i represents a specific energy of the X-ray energy spectrum, and x represents the second object thickness corresponding to the pixel.

6. An X-ray imaging method, comprising:

(a) performing a first object imaging process to obtain a first object image by detecting a plurality of X-rays passing through a first object in an field of view (FOV);

(b) performing a baseline imaging process to obtain a baseline image by detecting the X-rays when the first object is not in the FOV;

(c) performing a second object imaging process to obtain a second object image by detecting the X-rays passing through a second object in the FOV;

(d) obtaining a sample image based on the first object image and the second object image, wherein the first object is a carrier, and the second object comprises a sample and the carrier;

(e) obtaining a sample thickness based on the sample image, the baseline image and a sample attenuation coefficient;

(f) obtaining a number of residual photons base on the baseline image, the sample thickness, and a sample absorption coefficient; and (g) obtaining the number of absorbed photons in the sample based on the baseline image and the number of residual photons.

7. The X-ray imaging method of claim 6, wherein obtaining the sample thickness in step (e) comprises:

(e-1) obtaining a sample thickness characteristic curve by performing operations on the X-ray energy spectrum of the baseline image and the sample attenuation coefficient; and (e-2) obtaining the sample thickness by performing operations on the sample thickness characteristic curve and the sample image.

8. The X-ray imaging method of claim 6, further comprising step (h):

(h) calculating a absorbed energy per pixel based on the number of absorbed photons in the sample by a function, and the function is:

$$\text{Abosrbed Energy}_k = \sum_{i=1}^{E\,keV} i \times N_{abs_i} \times \left( \frac{1.6 \times 10 - 13\ J}{keV} \right)$$

wherein

E is a maximum voltage of the X-ray source, i is a specific energy of the X-ray energy spectrum, and $N_{abs_i}$ is the number of absorbed photons as the X-rays at the specific energy i of the X-ray energy spectrum passing along the sample thickness corresponding to a pixel k.

9. The X-ray imaging method of claim 6, further comprising a step (i):

(i) obtaining a weight of the sample corresponding to a pixel k in the FOV by performing operations on the sample thickness, a density of the sample and a pixel size.

10. An X-ray imaging system, comprising:

an X-ray source, configured to perform a first object imaging process so that a plurality of X-rays pass through a first object placed in a field of view (FOV) and perform a baseline imaging process as the first object is not in the FOV;

a detector, configured to detect the X-rays to obtain a baseline image in the baseline imaging process and obtain a first object image in the first object imaging process; and a processor, coupled to the detector; wherein the processor is configured to operate instructions, comprising: calculating a first thickness of the first object based on the first object image, the baseline image, and a first attenuation coefficient of the first object;

wherein the X-ray source is configured to further perform a second object imaging process so that the X-rays pass through a second object placed in the FOV;

the detector is configured to further obtain a second object image in the second object imaging process; and the processor is configured to operate instructions, further comprising: calculating a second thickness of the second object based on the second object image, the baseline image, and a second attenuation coefficient of the second object;

wherein the processor is configured to operate instructions, further comprising:

subtracting the first thickness from the second thickness to obtain a sample thickness;

obtaining a number of residual photons base on the baseline image, the sample thickness, and a sample absorption coefficient; and obtaining the number of absorbed photons in the sample based on the baseline image and the number of residual photons.

11. The X-ray imaging system of claim 10, wherein the processor is configured to operate instructions, further comprising:

obtaining a first thickness characteristic curve based on an X-ray energy spectrum of the baseline image and the first attenuation coefficient; and obtaining a second thickness characteristic curve based on the X-ray energy spectrum of the baseline image and the second attenuation coefficient.

\* \* \* \* \*